United States Patent [19]

Laird

[11] Patent Number: 4,871,879

[45] Date of Patent: Oct. 3, 1989

[54] RHODIUM RECOVERY FROM HYDROFORMYLATION REACTION PRODUCT

[75] Inventor: Keith A. Laird, Pampa, Tex.

[73] Assignee: Hoechst Celanese Corporation, Somerville, N.J.

[21] Appl. No.: 114,171

[22] Filed: Oct. 27, 1987

[51] Int. Cl.[4] .......................... B01D 3/34; C07C 45/50
[52] U.S. Cl. ..................... 568/454; 568/492; 203/49; 203/73; 203/74; 203/81; 203/DIG. 6
[58] Field of Search ................... 568/454, 492; 203/49, 203/DIG. 6, 74, 81, 73, 71

[56] References Cited

U.S. PATENT DOCUMENTS

| | | | |
|---|---|---|---|
| 1,833,717 | 11/1931 | Laird | 203/49 |
| 4,199,410 | 4/1980 | Ohrui et al. | 203/49 |
| 4,289,589 | 9/1981 | Koehler et al. | 203/49 |
| 4,479,012 | 10/1984 | Fischer et al. | 203/DIG. 6 |
| 4,593,127 | 6/1986 | Bunning et al. | 568/454 |
| 4,613,701 | 9/1986 | Strong | 203/62 |

OTHER PUBLICATIONS

Weissberger: Technique of Organic Chemistry vol. IV: Distillation; N.Y. 1951, pp. 377, 378.

*Primary Examiner*—Wilbur Bascomb
*Attorney, Agent, or Firm*—Depaoli & O'Brien

[57] ABSTRACT

In the hydroformylation of alkenes to aldehydes, rhodium is recovered from the stripped overhead of the hydroformylation reactor by condensing the overhead, removing the bulk of the aldehyde product from the condensed overhead, stripping the residue which remains with nitrogen gas to remove minor amounts of highly volatile aldehyde product remaining in the residue and redistilling the residue to remove components from the condensed overhead which are lower boiling than the catalyst components. The catalyst components including rhodium and phosphine ligand are returned to the hydroformylation reactor.

10 Claims, No Drawings

RHODIUM RECOVERY FROM HYDROFORMYLATION REACTION PRODUCT

BACKGROUND OF THE INVENTION

This invention relates to the hydroformylation of a lower alkene to produce an aldehyde having one carbon atom more than the alkene feedstock. The hydroformylation process comprises reacting a mixture of hydrogen and carbon monoxide with the alkene in the presence of a catalyst which comprises rhodium complexed with a triorganophosphine as exemplified by triphenylphosphine. The reaction is conducted in the presence of liquid reaction medium comprising a high-boiling solvent.

The invention is specifically directed to those reaction systems, which are well known in the pertinent prior art in which the hydrogen, carbon monoxide, and vapors of the alkene are sparged through the liquid reaction medium during the course of the reaction both to effect agitation of the reaction medium and also to strip out the aldehyde product as it is formed, in the vaporous mixture exiting the hydroformylation reactor.

The literature dealing with hydroformylation reaction systems of the type just described is voluminous. U.S. Pat. No. 3,527,809, to Pruett et al, provides a comprehensive discussion of the chemistry of these systems. U.S. Pat. No. 3,239,566, to Slaugh et al, is also pertinent as background for the basic process.

U.S. Pat. No. 4,151,209, to Paul et al, provides a discussion of product recovery by stripping of the liquid reaction medium and also discusses applicable high-boing reaction solvents. U.S. Pat. No. 4,480,138, to Hackman et al, also discusses especially useful reaction solvents and deals at considerable length with the technology of the product-stripping operation itself.

U.S. Pat. No. 4,148,830, to Pruett et al, teaches the use of high-boiling reaction by-products as the reaction solvent.

The recovery of the aldehyde product from the liquid reaction medium can be effected in a number of ways including continuously drawing off a slip stream from the hydroformylation reactor and distilling it to separate relatively low-boiling compounds including the aldehyde product as an overhead stream and then returning the stripped residue to the hydroformylation reactor as desired. Alternatively, the continuous stripping of the reaction medium by sparging hydrogen, carbon monoxide, and alkene vapors into the liquid contained in the hydroformylation reactor, with the only aldehyde product being continuously withdrawn from the top of the reactor in the exiting gases, is particularly useful when the aldehyde is of substantial volatility, as in the case of propionaldehyde and the butyraldehydes. The continuous hydroformylation of propylene in a gas-sparged reactor in this manner is discussed by Hershman et al in *Industrial and Engineering Chemistry Product Research and Development*, Vol. 8 (1969), pages 372–375.

U.S. Pat. No. 4,247,486, to Brewester et al, describes a system in which the gas recycle through the hydroformylation reactor is controlled in such a manner as to maintain the liquid level in the reactor and control the build-up of high molecular weight by-products.

The potential problem of loss of valuable rhodium in the reactor overhead in the form of entrainment is mentioned in U.S. Pat. No. 4,247,486, and also in U.S. Pat. No. 4,287,369, to Harris et al, who also describe a product-recovery system in which the gases exiting the hydroformylation reactor are subjected to condensation with non-condensed components being recycled to the hydroformylation reactor. Both U.S. Pat. No. 4,247,486 and U.S. Pat. No. 4,286,369 disclose the use of demisting pads through which the gases exiting the hydroformylation reactor are passed in order to remove entrained liquid droplets for return to the reactor. In neither case is there a suggestion that the demisting pads are in any way deficient in preventing loss of rhodium from the reaction system.

However, as disclosed in U.S. Pat. No. 4,613,701 to Strong, conventional entrainment separators such as demisting pads are not completely effective in preventing loss of rhodium into the reactor overhead system. Even small losses of rhodium through the entrainment-separation system are very significant economically because of the high cost of rhodium. Also, of course, rhodium is a strategically important metal regardless of its monetary cost. It is not known with certainty whether these loses of rhodium through the, for example, demisting pads occur as very fine entrainment which is not trapped by the pads or whether there is actually some volatilization of the rhodium as complexes which have an appreciable although certainly very low, volatility.

In accordance with the invention as disclosed in U.S. Pat. No. 4,613,701, the vapors which are stripped overhead with the aldehyde products in a hydroformylation reactor operating as previously described are condensed and then distilled to produce, a first distillate comprising the aldehyde hydroformylation product along with a first residue comprising substantially the entirety of those components of the hydroformylation product condensate which are less volatile than the aldehyde product. This first residue is then redistilled to separate it into (a) a redistillation overhead stream which comprises substantially the entirety of those compounds present which are more volatile than the ligand which is used in the hydroformylation catalyst system (typically and normally triphenylphosphine) and (b) a redistillation residue which comprises those components of the initially-obtained hydroformylation reaction product condensate which are equal to or lower than the ligand (typically triphenylphosphine) in volatility and which include any rhodium moiety which may have been initially present in the condensed hydroformylation reaction product vapors. The rhodium-containing residue from the second distillation not only contains substantially the entirety of the rhodium which was initially lost out the top of the hydroformylation reactor, but it also is substantially free of high-boiling reaction by-products which tend to deactivate the hydroformylation catalyst as they build up in the hydroformylation reactor. Free of these compounds, the residue obtained from the second distillation is suitable for recycle to the hydroformylation reactor as catalyst makeup.

Unfortunately, as recognized by Strong there still remains a small portion of aldehyde product in the first residue which is separated from the bulk of the aldehyde product. For certain aldehydes such as butyraldehyde this requires that the first residue which contains small quantities of butyraldehyde be distilled in two stages, a low temperature stage which avoids a temperature above 230° C. which is the auto-ignition point of butyraldehyde and a second high temperature stage to remove the other high-boiling heavy ends from the catalyst makeup residue. This "two-pass" operation needed to remove explosive aldehydes is cumbersome and not economical. It would be advantageous to recover the catalyst makeup residue in a single distillation and yet still run the distillation safely without the dangers of ignition of low boiling aldehyde products such as butyraldehyde. Such operation is the subject of this invention and forms its primary objective.

SUMMARY OF THE INVENTION

In accordance with the present invention, rhodium catalyst used in the hydroformylation of propylene to butyraldehyde and which is entrained in the stripped overhead containing the aldehyde products from the hydroformylation reactor is recovered in a novel manner which greatly reduces the possibility of auto-ignition of the butyraldehyde and allows for a single-pass distillation recovery of rhodium from the first residue obtained from the condensed overhead. It has been found that butyraldehyde can be removed from the distilled overhead residue by stripping the residue with nitrogen gas. The stripped residue is then redistilled in a single-pass operation to form the catalyst makeup residue which comprises components of the initially-obtained hydroformylation reaction product condensate which are equal to or lower than the phosphine ligand in volatility and which include any rhodium moiety which may have been initially present in the condensed hydroformylation reaction product vapors. The rhodium-containing residue from the distillation is essentially free of the butyraldehyde and is substantially free of high-boiling reaction byproducts which tend to deactivate the hydroformylation catalyst as a build up in the hydroformylation reactor. The process of the present invention thus, eliminates the need of a two-pass recovery distillation process as previously suggested in U.S. Pat. No. 4,613,701 and thus, can be run more safely and economically to provide rhodium recovery.

DETAILED DESCRIPTION

The invention is not restricted in its applicability to hydroformylation reaction systems employing any particular reaction solvent, although it is especially useful in systems in which the reaction solvent is either a high-molecular weight polyalkylene glycol or else a high molecular weigh alkane, including especially linear alkanes. If desired, it can also be employed with systems in which the hydroformylation reaction solvent comprises high molecular weight by-products of the hydroformylation reaction itself. Broadly speaking, the fundamental principle is also applicable to reaction systems, as known in the art, in which the aldehyde product is recovered by redistilling a slipstream drawn from the liquid contained in the hydroformylation reactor. That is systems which use a liquid drawoff from the reactor rather than recovering the aldehyde product from vapors withdrawn from the head of the reactor. In this latter adaptation, the problem, being addressed is not the escape of rhodium from the reactor in vapors which are withdrawn from its head. Rather, the problem is recovering the rhodium in condition fit for recycle to the hydroformylation reactor substantially free from catalyst deactivators which, it has been discovered, boiled at a temperature slightly lower than the boiling point of the reaction ligand, (e.g., triphenylphosphine). In this particular embodiment care is taken to include a step in the series of distillations used to work up the crude reaction product wherein there is distilled overhead, and away from a rhodium-containing residue, a cut which boils just before the reaction ligand. Care is taken not to return this cut to the hydroformylation reaction system.

The invention is broadly applicable to systems in which any alkene, more particularly any alpha-alkene, having from 2 to about 10 carbon atoms is hydroformylated in accordance with the prior-art practices previously discussed hereinabove to produce an aldehyde having one carbon atom more than the alkene. It is particularly useful, however, in processes for converting propylene to butyraldehydes including especially n-butyraldehyde. As previously explained, these processes use a high-boiling liquid reaction solvent and a rhodium-complex catalyst wherein the ligand is typically a phosphine, especially triphenylphosphine. In particular, the present invention is directed to that operating mode in which a gaseous mixture comprising carbon monoxide, hydrogen, and the alkene being hydroformylated is continuously bubbled through the liquid reaction medium containing the catalyst, with the aldehyde product, as it is formed being continuously removed from the head of the reactor in a stream of the gas which has passed through the reaction medium. The gas is passed through the reaction medium at such a rate as to maintain a constant liquid level in the reactor. The total reactor pressure is normally about 5 to 40 atmospheres, and the reaction temperature is approximately 80° to 150° C. The concentration of rhodium in the liquid reaction medium is typically about 500 to 1400 ppm calculated as rhodium. The rate of gas reactor throughput is not critical to the purposes of the present invention, but typical industrial applications entail gas throughput rates such that the total volume of gases and vapors, including both fixed gases and condensable vapors, leaving the head of the hydroformylation reactor is about 0.5 to 7.5 volumes of total gases and vapors per minute (measured at reaction temperature and pressure) per volume of liquid contained in the hydroformylation reactor.

As previously mentioned, until U.S. Pat. No. 4,613,701, the prior art was not unacquainted with the fact that there is some danger of the entrainment of rhodium into the gases leaving the hydroformylation reactor. The invention disclosed in U.S. Pat. No. 4,613,701 was based on the discovery that the problem is greater than previously realized. It was also based in part on the discovery that over and above the rhodium-entrainment problem, there is also a catalyst deactivation problem associated with the buildup of high-boiling reaction by-products which are more volatile that the reaction ligand which is being employed but less volatile than the aldehyde product and the intermediate reaction by-products boiling just above the aldehyde. The present invention is an improvement over U.S. Pat. No. 4,613,701 as it achieves the same objectives as described above but, in a more economical and safe manner.

Broadly speaking, the present invention comprises redistilling the crude product condensate formed by condensing the vapors drawn off from the head of the hydroformylation reactor to separate it into a light cut comprising the aldehyde product, a cut comprising the compounds which are less volatile than the aldehyde product but more volatile than the reaction ligand (typically triphenylphosphine) and a final residue comprising those components of the original crude reaction product condensate which are equal to or lower than triphenylphosphine in volatility and which includes the rhodium. Although this can be accomplished if desired in an arrangement of continuously-operating distillation towers, it is convenient to recover the aldehyde and those compounds boiling close to it in a continuous primary distillation of the crude hydroformylation reaction product condensate, with the higher-boiling compounds remaining after the removal of the aldehyde being then worked up in a batch distillation. The initial distillation of the reaction product condensate to recover a distillate comprising the bulk of the aldehyde formed in the hydroformylation reaction entails obvious distillation techniques well known to those skilled in the art. Details of the present invention are largely concerned with the workup of the crude reaction heavy ends mixture which remains as a residue after the bulk of the aldehyde product has been distilled out of the initial crude reaction product condensate. That is the present invention is concerned with working up the heavy ends remaining after the bulk of the aldehyde product has been separated for further purification by conventional methods which are known in the art. Some aldehyde typically remains in these heavy ends, of course, and is recovered from them in the present process before further processing of the residues to remove deleterious high-boiling by-products and recover a final stripped residue which contains the rhodium and is suitable for recycle to the hydroformylation reactor.

Advantageously the present process is applied to the residue which remains after the hydroformylation reactor condensate product has been distilled to recover substantially the entirety of the aldehyde hydroformylation product and those compounds which are close to it in boiling point (e.g., the corresponding alcohol). As previously explained, distillation of the reaction product condensate to recover the aldehyde product involves known technology and is an inherent part of any hydroformylation process entailing removal of the product from the hydroformylation reactor in the vapor phase. The present invention is directed primarily to processing the residue which remains after the bulk of the aldehyde product has been separated.

In accordance with the present invention, the residue is first treated to remove highly volatile, if not explosive, aldehydes which remain in the residue prior to distilling the residue to separate the deleterious high-boiling by-products which are more volatile than the reaction ligand but less volatile than the aldehyde product. The invention is particularly useful in removing butyraldehyde from the residue so that the residue can be distilled in a single-pass operation to recover the catalyst makeup stream which contains the rhodium catalyst. Removal of the aldehyde from the residue is achieved by stripping the residue with nitrogen gas. It has been found that nitrogen gas will remove the butyraldehyde from the residue and, thus, removes the autoignition possibility when the residue is distilled to recover the rhodium. The nitrogen stripping is carried out at low positive pressures ranging from about 1 atmosphere to 5 atmospheres, and preferable from 1 to 2 atmospheres. The stripping process does not require any additional heat input and, thus, can be run at approximately room temperature. Any known stripping column can be utilized to achieve nitrogen stripping of the aldehyde from the residue and those of ordinary skill in the art will recognize the pertinent apparatus.

Typically, the liquid residue feed rate will range from about 100 to 400 pounds per hour while the nitrogen feed will vary from about 15 to 200 pounds per hour. The stripping column will typically be a packed column in which the liquid is trickled through the bed while the nitrogen flow is run countercurrent relative to the liquid flow through the bed.

Once stripped of the highly volatile aldehyde product, the residue can be distilled as described in U.S. 4,613,701. The redistillation of the present rhodium-recovery system does not require careful fractionation and can be carried out in a simple flasher, although a few fraction trays of a type adapted to very low pressure-drop operation will help in obtaining sharp separations. However, because the desired rhodium-containing residue product is so very low in volatility, a simple vacuum flash without trays is satisfactory and economical, There are, however, certain operating controls which should be maintained. While higher temperatures up to about 260° C. can be employed once the butyraldehyde or other highly volatile aldehydes are removed by $N_2$ stripping, above 260° C. there is danger that deactivation of the rhodium catalyst in the stillpot may take place. Broadly, operating stillpot temperatures will be between about 150° C. and 260° C. with temperatures between 205° C. and 232° C. being preferred. Operating pressure is preferably between about 10 mm HgA and 25 mm HgA in the "single-pass" mode of operation. By "single-pass" operation is meant distilling overhead substantially everything boiling lower than the ligand (e.g. triphenylphosphine), with the resulting distillate being further processed as desired while the residue is suitable for recycle to the hydroformylation reactor.

EXAMPLE

Propylene is hydroformylated in a polyalkylene glycol reaction solvent. The catalyst comprises rhodium complexed with triphenylphosphine ligand. The product is continuously removed from the hydroformylation reactor in the vapor phase in a stream of gas comprising carbon monoxide, hydrogen, and propylene which is continuously bubbled through the liquid contained in the hydroformylation reactor and then removed from the top of the reactor carrying with it the butyraldehyde product in vapor form. The gases evolving from the top of the hydroformylation reactor are passed through a condenser to recover a crude hydroformylation reaction product condensate which is then redistilled to recover the bulk of the butyraldehyde for further processing outside the scope of the present invention. The residues remaining after removal of the butyraldehyde product contain substantially the entirety of everything boiling above about 384° C. at atmospheric pressure which was initially contained in the crude hydroformylation reaction condensate. In particular, this heavy ends residue after butyraldehyde removal contains, in addition to minor amounts of butyraldehyde and butanol, substantial proportions of 2-ethylhexanal, 2-ethylhexenal, butyrates, triorganophosphines, and heavy ends including quantities of the hydroformylation reaction solvent. It also contains about 70 ppm of rhodium even though the gases leaving the hydroformylation reactor have passed through about 4 feet of "Koch-Sulzer" (Koch Engineering Co.) mist-eliminating packing irrigated with liquid reflux at about 0.334 liters of liquid per square meter of packed cross-section per second.

The approximate analysis of this heavy ends residue by weight is as follows:

| | |
|---|---|
| Butyraldehydes | 0.5% |
| Butanol | 9.1% |
| 2-Ethylhexanal | 28.6% |
| 2-Ethylhexenal | 22.3% |
| Butyl Butyrates | 15.7% |
| Phosphines | 14.5% |
| Heavy Ends | 9.3% |
| Rhodium | 70 ppm |

The rhodium-containing residue just described is passed (200.9 lbs/hr) to the top of a butyraldehyde stripper. The stripper is a packed tower, 4 in. in diameter, and 12 ft. high. The tower is packed with ⅜ in. 316 SS Raschig rings. Temperature of the residue is 295° F. at 25 psia. Directed to the stripper for countercurrent flow with the residue is 50.1 lbs per hour of nitrogen gas at a temperature of 80° F. and at 140 psia.

The analysis of the stripper vapor leaving the top of the stripper and analysis of the residue are given below:

| STRIPPED VAPOR | lbs/hr. | Weight % |
|---|---|---|
| Butyraldehydes | 1.0 | 1.1 |
| Butanol | 10.3 | 10.9 |
| 2-Ethylhexanal | 5.1 | 5.4 |
| 2-Ethylhexenal | 12.2 | 12.9 |
| Butyl Butyrates | 16.2 | 17.0 |
| Phosphines | — | — |
| Heavy Ends (Others) | — | — |
| Air | — | — |
| Nitrogen | 50.1 | 52.8 |
| Total | 94.9 | 100.1 |
| RESIDUE | lbs/hr. | Weight % |
| Butyraldehydes | — | — |
| Butanol | 8.0 | 5.1 |
| 2-Ethylhexanal | 52.3 | 33.5 |
| 2-Ethylhexenal | 32.6 | 20.9 |
| Butyl Butyrates | 15.3 | 9.8 |
| Phosphines | 29.2 | 18.7 |
| Heavy Ends (Others) | 18.7 | 12.0 |
| Air | — | — |
| Nitrogen | — | — |
| Total | 156.1 | 100.0 |

What is claimed is:

1. In a process for catalytically hydroformylating propylene by the following steps: (a) reacting said propylene with carbon monoxide and hydrogen in the presence of a liquid reaction medium containing as the hydroformylation catalyst a complex of rhodium with a triorganophosphine to produce a liquid reaction mixture comprising triorganophosphine, butyraldehyde, and reaction by-products; (b) stripping said liquid reaction mixture by gas stripping, distillation, or evaporation during the course of said hydroformylation reaction to remove a vapor stream comprising said butyraldehyde and said hydroformylation catalyst overhead from said reaction mixture; (c) condensing said vapor stream and recovering a crude product condensate comprising said butyraldehyde; (d) distilling said condensate to form a distillate comprising the bulk of said butyraldehyde from said condensate and a residue comprising a crude reaction heavy ends mixture containing a minor amount of said butyraldehyde; and (e) distilling said crude reaction heavy ends mixture into (1) an overhead stream comprising those components of the crude reaction heavy ends mixture which are more volatile than said triorganophosphine and (2) a residue stream comprising those components of the crude reaction heavy ends mixture which are equal to or lower than said triorganophosphine in volatility and including any rhodium moiety initially contained in said vapor stream, the improvement which comprises:

prior to step (e), stripping said residue containing said crude reaction heavy ends mixture obtained from step (d) with nitrogen gas to remove therefrom said minor amount of butyraldehyde.

2. The improvement of claim 1 wherein said liquid reaction medium comprises a high-boiling inert liquid solvent.

3. The improvement of claim 1 wherein the pressure during stripping said crude reaction heavy ends mixture ranges from about 1 to about 5 atmospheres.

4. The improvement of claim 3 wherein said pressure ranges from about 1 to about 2 atmospheres.

5. The improvement of claim 1 wherein said crude reaction heavy ends mixture is distilled at a temperature of between about 150° to 260° C. in step (c).

6. The improvement of claim 1 wherein said crude reaction heavy ends mixture is distilled in step (e) in a single pass operation wherein substantially all components of said crude reaction heavy ends mixture boiling lower than said triorganophosphine are removed overhead in a single step.

7. The improvement of claim 1 wherein said propylene is reacted with carbon monoxide and hydrogen at a temperature of about 80° C. to about 150° C. in step (a).

8. The improvement of claim 1 wherein said triorganophosphine is triphenylphosphine.

9. The method of claim 1 wherein said stripping of the residue containing said crude reaction heavy ends mixture is conducted in a packed column with countercurrent flow of said residue and nitrogen gas.

10. The method of claim 9 wherein said nitrogen gas is fed to said stripper at a rate of from about 15 to 200 pounds per hour.

* * * * *

UNITED STATES PATENT AND TRADEMARK OFFICE
CERTIFICATE OF CORRECTION

PATENT NO. : 4,871,879
DATED      : October 3, 1989
INVENTOR(S) : Laird, Keith A.

It is certified that error appears in the above—identified patent and that said Letters Patent is hereby corrected as shown below:

Column 8 Line 34  - "in step (c)" should read "in step (e)."

Signed and Sealed this

Twenty-second Day of December, 1992

Attest:

DOUGLAS B. COMER

Attesting Officer    Acting Commissioner of Patents and Trademarks